United States Patent [19]

Berg

[11] Patent Number: 5,928,478
[45] Date of Patent: Jul. 27, 1999

[54] SEPARATION OF LINOLEIC ACID FROM LINOLENIC ACID BY AZEOTROPIC DISTILLATION

[76] Inventor: Lloyd Berg, 1314 S. 3rd Ave., Bozeman, Mont. 59715

[21] Appl. No.: 09/152,891

[22] Filed: Sep. 14, 1998

[51] Int. Cl.⁶ .............................. B01D 3/36; C07C 51/46
[52] U.S. Cl. .............................. 203/57; 203/60; 203/62; 554/185; 554/186
[58] Field of Search .................. 203/57, 60, 67, 203/58, 62; 554/185, 186, 206, 212

[56] References Cited

U.S. PATENT DOCUMENTS

| | | | |
|---|---|---|---|
| 2,200,390 | 5/1940 | Freeman | 554/13 |
| 2,200,391 | 5/1940 | Freeman | 554/14 |
| 3,892,789 | 7/1975 | Parsons | 554/185 |
| 5,084,142 | 1/1992 | Berg et al. | 203/57 |
| 5,085,739 | 2/1992 | Berg et al. | 203/60 |

*Primary Examiner*—Virginia Manoharan

[57] ABSTRACT

Linoleic acid cannot be separated from linolenic acid by distillation or rectification because of the closeness of their boiling points. Linoleic acid is readily separated from linolenic acid by azeotropic distillation. Effective agents are nonane, dimethyl formamide, 2-nitropropane and pentyl propionate.

2 Claims, No Drawings

SEPARATION OF LINOLEIC ACID FROM LINOLENIC ACID BY AZEOTROPIC DISTILLATION

FIELD OF THE INVENTION

This invention relates to a method for separating linoleic acid from linolenic acid using certain organic liquids as the agent in azeotropic distillation.

DESCRIPTION OF PRIOR ART

Azeotropic distillation is the method of separating close boiling compounds or azeotrones from each other by carrying out the distillation in a multiplate rectification column in the presence of an added liquid, said liquid forming an azeotrope with one or more of the compounds to be separated. It presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in reddjative volatility of the compounds to be separated. Table 1 shows the degree of separation or purity obtainable by theoretical plates at several relative volatilites. Table 1 shows that a relative volatility of at least 1.2 is required to get an effective separation by rectification.

TABLE 1

Effect Of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Refux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Linoleic acid and linolenic acid boil only one degree apart and have a relative volatility of 1.05 which makes it impossible to separate them by conventional distillation or rectification. Table 2 shows that with an agent giving a relative volatility of 1.4, only 35 actual plates are required to get 99% purity.

TABLE 2

Theoretical And Actual Plates Required vs. Relative Volatility For Linoleic Acid From Linolenic Acid Separation

| Relative Volatility | Theoretical Plates Required At Total Reflux, 99% Purity | Actual Plates Required, 75% Efficiency |
|---|---|---|
| 1.16 | 62 | 83 |
| 1.27 | 39 | 52 |
| 1.35 | 31 | 41 |
| 1.40 | 26 | 35 |

OBJECTIVE OF THE INVENTION

The objectof this invention is to provide a process or method of azeotropic distillation that will enhance the relative volatility ot linoleic acid from linolenic acid in their separation in a rectification column. It is a further object of this invention to identify effective azeotropic distillation agents that are stable and can be recyled.

SUMMARY OF THE INVENTION

The objects of this invention are provided by a process for the separation of linoleic acid from linolenic acid which entails the use of certain organic compounds when employed as the agent in azeotropic distillation.

TABLE 3

Effective Azeotropic Distillation Agents For Separating Linoleic Acid From Linolenic Acid

| Compounds | Relative Volatility |
|---|---|
| None | 1.05 |
| Dimethyl formamide | 1.35 |
| Ethyl acetate | 1.17 |
| 2-Nitropropane | 1.27 |
| 1-Methyl-2-pyrrolidinone | 1.16 |
| Nonane | 1.4 |

TABLE 4

Effective Azeotropic Distillation Agents For Separating Linolenic Acid From Linoleic Acid

| Compounds | Relative Volatility |
|---|---|
| None | 1.05 |
| Pentyl propionate | 1.27 |
| Propiophenone | 1.17 |

DETAILED DESCRIPTION OF THE INVENTION

I have discovered that certain organic compounds will effectively increase the relative volatility between linoleic acid and linolenic acid during rectification when employed as the agent in azeotropic distillation. They are dimethyl formamide, ethyl acetate, 2-nitro- propane, 1-methyl-2-pyrtolidinone, nonane, pddlntyl propionate, and propiophenone.

THE USEFULNESS OF THE INVENTION

The usefulness of this invention can be demonstrated by referring to the data presented in Tables 1, 2, 3 and 4. All of the successful agents show that linoleic acid can be separated from linolenic acid by means of azeotropic distillation in a rectification column and that the ease of separation as measured by relative volatility is considerable.

WORKING EXAMPLE

1. Fifty grams of linoleic—linolenic acids and fifty grams of nonane were charged to a vapor—liquid equilibrium still and refluxed for two hours. The vapor composition was 64.5% linoleic acid and 35.5% linolenic acid. The liquid composition was 56.2% linoleic acid and 43.8% linolenic acid. This is a relative volatility of 1.4. 2. Fifty grams of linolenic—linoleric acids and fifty grams of pentyl propionate were charged to a vapor—liquid equilibrium still and refluxed for two hours. The vapor composition was 61.1% linolenic acid and 38.9% linolenic acid. The liquid composition was 55.2 linolenic acid and 44.9% linoleric acid. This is a relative volatility of 1.27.

I claim:

1. A method for recovering linoleic acid from linolenic acid which comprises distilling a mixture of linoleic acid and linolenic acid in the presence of an azeotrocde forming agent, recovering the linoleic acid and the azeotrope forming agent as overhead product and obtaining the linolenic acid as bottoms product, wherein said azeotrope forming agent consists essentially of one material selected from the group consisting of ethyl acetate and 2-nitropropane.

2. A method for recovering linolenic acid from linoleic acid which comprises distilling a mixture of linolenic acid and linoleic acid in the presence of an azeotropic forming agent, recovering the linolenic acid and the azeotrope forming agent as overhead product and obtaining the linoleic acid as bottoms product, wherein said azeotrope forming agent consists essentially of one material selected from the group consisting of pentyl propionate and propiophenone.

* * * * *